United States Patent
Yang et al.

(10) Patent No.: US 10,993,937 B2
(45) Date of Patent: May 4, 2021

(54) COMPOSITION, FOR PREVENTING OR TREATING DRY EYE SYNDROME, CONTAINING POLYETHYLENE GLYCOL AND FLAVONOID NANOCOMPOSITE AS ACTIVE INGREDIENT

(71) Applicant: INJE UNIVERSITY INDUSTRY-ACADEMIC COOPERATION FOUNDATION, Gimhae-si (KR)

(72) Inventors: Jae Wook Yang, Busan (KR); Hye Sook Lee, Busan (KR); Yoon Jin Lee, Busan (KR); Chae Eun Kim, Busan (KR); Hae Shin Lee, Daejeon (KR); Whui Su Shim, Icheon-si (KR); Moon Sue Lee, Seoul (KR)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 0 days.

(21) Appl. No.: 16/488,940

(22) PCT Filed: Aug. 2, 2017

(86) PCT No.: PCT/KR2017/008332
§ 371 (c)(1),
(2) Date: Aug. 27, 2019

(87) PCT Pub. No.: WO2018/155773
PCT Pub. Date: Aug. 30, 2018

(65) Prior Publication Data
US 2019/0374531 A1    Dec. 12, 2019

(30) Foreign Application Priority Data

Feb. 27, 2017  (KR) .................. 10-2017-0025467
May 10, 2017  (KR) .................. 10-2017-0058062

(51) Int. Cl.
| | | |
|---|---|---|
| A61K 31/353 | (2006.01) | |
| A61K 47/10 | (2017.01) | |
| A61K 47/60 | (2017.01) | |
| A61K 31/47 | (2006.01) | |
| A61K 9/00 | (2006.01) | |
| A61K 9/06 | (2006.01) | |
| A61K 45/06 | (2006.01) | |

(52) U.S. Cl.
CPC ............ *A61K 31/47* (2013.01); *A61K 9/0048* (2013.01); *A61K 9/06* (2013.01); *A61K 31/353* (2013.01); *A61K 47/10* (2013.01); *A61K 47/60* (2017.08); *A61K 45/06* (2013.01)

(58) Field of Classification Search
CPC ...... A61K 31/353; A61K 47/10; A61K 47/60; A61K 9/06
See application file for complete search history.

(56) References Cited

U.S. PATENT DOCUMENTS

| | | |
|---|---|---|
| 2005/0220753 A1 | 10/2005 | Ji et al. |
| 2014/0294986 A1 | 10/2014 | Liu et al. |
| 2017/0258926 A1 | 9/2017 | Kurisawa et al. |

FOREIGN PATENT DOCUMENTS

| | | |
|---|---|---|
| KR | 10-2015-0139899 A | 12/2015 |
| KR | 10-2017-0007780 A | 11/2017 |

OTHER PUBLICATIONS

Naomasa et al. (JP 2002326941 A, 2002, pp. 1-6, English Translation).*
International Search Report for PCT/KR2017/008332 dated Nov. 29, 2017 from Korean Intellectual Property Office.
Shin, M. et al., "Tannic Acid as a Degradable Mucoadhesive Compound", ACS Biomaterials Science & Engineering, 2016, vol. 2, pp. 687-696.
Lee, H. et al., "Therapeutic Efficacy of Nanocomplex of Poly(Ethylene Glycol) and Catechin for Dry Eye Disease in a Mouse Model", Investigative Ophthalmology & Visual Science, Mar. 2017, vol. 58, No. 3, pp. 1682-1691.

* cited by examiner

*Primary Examiner* — Samira J Jean-Louis
(74) *Attorney, Agent, or Firm* — Revolution IP, PLLC (57) ABSTRACT

A composition for preventing or treating dry eye syndrome includes nanocomposite of a polyethylene glycol and a flavonoid as an active ingredient, and in the present invention, a catechin/PEG nanocomposite having increased catechin bioavailability is prepared by using catechins which are an antioxidant and polyethylene glycol which is a hydrophilic polymer used in a drug delivery system, and an increase in tear generation, stabilization of corneal epithelial cells, an increase in conjunctival goblet cells and enhanced anti-inflammatory effects accordance to a PEG dosage by the catechin/PEG nanocomposite are confirmed in a mouse model with dry eye syndrome.

11 Claims, 8 Drawing Sheets

COMPOSITION, FOR PREVENTING OR TREATING DRY EYE SYNDROME, CONTAINING POLYETHYLENE GLYCOL AND FLAVONOID NANOCOMPOSITE AS ACTIVE INGREDIENT

CROSS REFERENCE TO PRIOR APPLICATIONS

This application is a National Stage Application of PCT International Patent Application No. PCT/KR2017/008332 filed on Aug. 2, 2017, under 35 U.S.C. § 371, which claims priority to Korean Patent Application Nos. 10-2017-0058062 and 10-2017-0025467 filed on May 10, 2017 and Feb. 27, 2017, respectively, which are all hereby incorporated by reference in their entirety.

TECHNICAL FIELD

The present invention relates to a composition for preventing or treating dry eye syndrome comprising a polyethylene glycol and a flavonoid nanocomposite as an active ingredient.

BACKGROUND ART

Dry eye syndrome is a disease of the tear and ocular surface, including imbalance, hyperosmotic pressure and inflammatory damage of the tear film. Inflammation is a major factor in ocular dryness, leading to a vicious cycle of eye surface damage including progressive dysfunction of the lacrimal glands and conjunctival epithelial damage. Accordingly, the use of anti-inflammatory agents is most commonly used among the various treatment options for treating ocular dryness.

Catechin (flavan-3-ol) belongs to flavonoids and is a natural antioxidant found in various fruits, beverages and tea. Recent reports of beneficial effects including antibacterial, anticarcinogenic, and anti-inflammatory properties of catechins have received attention. Previous studies have shown that epigallocatechin gallate (EGCG), a catechin derivative, is effective in the treatment of ocular diseases including dry eye, glaucoma and various retinal dysfunctions through anti-inflammatory and antioxidative effects. In addition, it has been reported that EGCG inhibits pro-inflammatory mediators in a mouse model of dry eye. However, only clinical findings using fluorescein staining were confirmed, and pathogenicity such as inflammation, lymphangiogenesis and apoptosis was evaluated in corneal epithelial cells in vitro. Catechins are powerful antioxidants, but catechins are limited in their use because of their low solubility in water, low bioavailability and their tendency to act as oxidation promoters depending on the dosage. Currently, research has been reported that increasing the molecular weight of catechins improves biological properties by increasing circulation time in the body.

Poly(ethylene glycol) (PEG) is a non-ionic and hydrophilic polymer widely used in various therapeutic biological drugs as a drug delivery system. PEG-based copolymers have biocompatibility, biodegradability and thermosensitivity and play a potential role as biomedical materials for biomedical applications because these properties can be easily controlled. According to a study published in 2008, possibility of nanocomplex of PEG and biopolymers (proteins, DNA, carbohydrates, etc.) has been reported as biological, long-acting and sustained-release formulations for therapeutic biological drug. In addition, PEG-based bipolar nanoparticles have been reported to be used so as to overcome multidrug resistance in cancer cells through the development of new drug delivery systems. However, most studies of PEG are limited to material engineering approaches, and the research on the efficacy of PEG is still unsatisfactory. A study published in 2014 reported the use of lipid nanoparticles as drug delivery vehicles. This study reported that EGCG encapsulated in lipid nanoparticles inhibits the oxidation and epimerization of drugs.

Nevertheless, studies on catechin and catechin/PEG nanocomposites in mouse model of dry eye have not been reported to date. In the present invention, PEG increases bioavailability of catechin, and catechin/PEG nanocomposite is expected to have synergistic effect and therapeutic effect in treating dry eye syndrome by improving anti-inflammatory effect of catechin.

DISCLOSURE

Technical Problem

It is an object of the present invention to provide a method of preparing a nanocomposite comprising a flavonoid and a polyethylene glycol and a pharmaceutical composition for preventing or treating dry eye syndrome comprising the nanocomposite as an active ingredient.

Technical Solution

In order to achieve the above object, the present invention provides a pharmaceutical composition for preventing or treating dry eye syndrome comprising a nanocomposite composed of a flavonoid and a polyethylene glycol as an active ingredient.

Also, the present invention provides a method of preparing a nanocomposite composed of a flavonoid and a polyethylene glycol comprising: a first step of preparing a flavonoid solution by dissolving a flavonoid in a C1 to C4 alcohol; a second step of preparing a polyethylene glycol solution by dissolving polyethylene glycol in water; a third step of preparing a mixture by mixing the flavonoid solution of the first step and the polyethylene glycol solution of the second step; a fourth step of removing the C1 to C4 alcohol from the mixture; and a fifth step of filtering the mixture from which the C1 to C4 alcohol is removed by a filter.

Advantageous Effects

In the present invention, a catechin/PEG nanocomposite having increased bioavailability of catechin was prepared using catechin which is an antioxidant and polyethylene glycol (PEG) which is a hydrophilic polymer used in a drug delivery system. It was confirmed in the mouse model of dry eye syndrome, that the catechin/PEG nanocomposite increased tear production, stabilized corneal epithelial cells, increased conjunctival epithelial cells and improved anti-inflammatory effect according to PEG dose.

Therefore, the catechin/PEG nanocomposite having the above effect can be utilized as a new biomedical material for treating dry eye syndrome through stabilization of the tear film and inflammation inhibition.

BEST MODE

The inventors of the present invention have confirmed that the drying stress induces the decrease of the tear production, the increase of corneal disorder, the increase of corneal epithelial cells detachment, the reduction of conjunctival goblet cells and the expression of inflammation-related factors, and the catechin/PEG nanocomposite is conformed to increase the tear production, stabilize the corneal epithelial cells, increase the conjunctival epithelial cells and improve anti-inflammatory effect according to PEG dose and completed the present invention.

The present invention provides a pharmaceutical composition for preventing or treating dry eye syndrome comprising a nanocomposite composed of a flavonoid and a polyethylene glycol as an active ingredient.

Preferably, the nanocomposite may be represented by the following Chemical Formula 1:

[Chemical Formula 1]

wherein $R_1$ to $R_4$ can be the same or different from each other and are hydrogen or a flavonoid, and m is any one integer of 8 to 460.

Preferably, the flavonoid may be selected from the group consisting of catechin, quercetin, baicalein, gallocatechin gallate, taxifolin, myricetin, morin and fisetin, but it is not limited thereto.

Preferably, the nanocomposite may be prepared by mixing a flavonoid solution and a polyethylene glycol solution at a weight ratio of 1:1 to 15, but it is not limited thereto.

Preferably, the number average molecular weight of the polyethylene glycol may be 400 to 20,000 g/mol, but it is not limited thereto.

Preferably, the average diameter of the nanocomposite may be 100 to 200 nm, but it is not limited thereto.

Preferably, the nanocomposite may increase the tear production and the density of conjunctival goblet cells.

Preferably, the nanocomposite may reduce the corneal epithelial cell detachment, the adhesion molecules, the pro-inflammatory cytokines and the matrix metalloproteinases (MMP).

Preferably, the adhesion molecules may be intercellular adhesion molecule-1 (ICAM-1) and vascular cell adhesion molecule-1 (VCAM-1), and the pro-inflammatory cytokines may be TNF-α, IL-1β, IL-6 and IL-17, and the matrix metalloproteinases may be MMP-2 and MMP-9, but it is not limited thereto.

Preferably, the pharmaceutical composition may be provided by mixing the nanocomposite with a pharmaceutically acceptable carrier and providing the composition as eye drugs or injections in form of eye drops, or eye ointment or injection in form of gel, but it is not limited thereto.

The pharmaceutical composition may be any one formulation selected from the group consisting of eye-drops, injections, granules, tablets, pills, capsules, gels, syrups, suspensions, emulsions, drops and liquids, but it is not limited thereto.

The pharmaceutical composition may comprise at least one additive selected from the group consisting of carriers, excipients, disintegrants, sweeteners, coatings, swelling agents, slip modifiers, flavors, antioxidants, buffers, bacteristats, diluents, dispersants, surfactants, binders and lubricants, which is suitably used for the preparation of a pharmaceutical composition.

Examples of the carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. Solid formulations for oral administration include tablets, pills, powders, granules, capsules, etc., and such solid formulations may contain at least one excipient such as starch, calcium carbonate, sucrose or lactose, gelatin and the like in addition to the composition. Furthermore, in addition to simple excipients, lubricants such as magnesium stearate and talc are also used. Examples of the liquid formulations for oral administration include suspensions, solutions, emulsions, syrups and the like, and various excipients such as wetting agents, sweeteners, fragrances, preservatives and the like may be included in addition to water and liquid paraffin which are commonly used as simple diluents. Formulations for parenteral administration include sterile aqueous solutions, non-aqueous solutions, suspensions, emulsions, freeze-dried preparations, suppositories and the like. Examples of the non-aqueous solution and the suspension include propylene glycol, polyethylene glycol, vegetable oil such as olive oil, injectable ester such as ethyl oleate, and the like. As the base of the suppository, witepsol, macrogol, tween 61, cacao butter, laurinum, glycerogelatin and the like can be used.

In addition, the pharmaceutical composition may be administered intravenously, intraperitoneally, intramuscularly, intraarterially, intrasternally, transdermally, nasally, inhaled, topically, rectally, orally, intraocularlly or intradermally to the subject in a conventional manner.

The dose may vary depending on the condition and body weight of the subject, the type and degree of the disease, the drug form, the administration route and the period, and may be appropriately selected by those skilled in the art. The administration may be performed once a day or in divided into several times, and thus the scope of the present invention is not limited thereto.

Also, the present invention a method of preparing a nanocomposite composed of a flavonoid and a polyethylene glycol comprising: a first step of preparing a flavonoid solution by dissolving a flavonoid in a C1 to C4 alcohol; a second step of preparing a polyethylene glycol solution by dissolving polyethylene glycol in water; a third step of preparing a mixture by mixing the flavonoid solution of the first step and the polyethylene glycol solution of the second step; a fourth step of removing the C1 to C4 alcohol from the mixture; and a fifth step of filtering the mixture from which the C1 to C4 alcohol is removed by a filter.

Preferably, the nanocomposite may be represented by a following Chemical Formula 1:

[Chemical Formula 1]

wherein $R_1$ to $R_4$ can be the same or different from each other and are hydrogen or a flavonoid, and m is any one integer of 8 to 460.

Preferably, the flavonoid may be selected from the group consisting of catechin, quercetin, baicalein, gallocatechin gallate, taxifolin, myricetin, morin and fisetin, but it is not limited thereto.

Preferably, in the third step, the flavonoid solution and the polyethylene glycol solution may be prepared by mixing at a weight ratio of 1:1 to 15, but it is to not limited thereto.

Preferably, the fourth step may be performed at 40 to 60° C. for 1 to 3 hours, but it is not limited thereto.

Preferably, the nanocomposite may have an average diameter of 100 to 200 nm, but it is not limited thereto.

Hereinafter, the present invention will be described in detail with reference to the following examples. The examples are only for describing the present invention in more detail and it is obvious to those skilled in the art that that the scope of the present invention is not limited by these examples embodiments in accordance with the gist of the present invention.

Example 1: Preparation of Catechin/PEG Nanocomposite

Catechin and polyethylene glycol (PEG) having an average molecular weight of 4,600 g per mole, were purchased from Sigma-Aldrich (St. Louis, Mo., USA) and methanol was purchased from Merck Millipore (Temecula, Calif., USA).

Catechin and PEG solutions were prepared separately prior to the preparation of a complex. First, catechin was dissolved in methanol to prepare a concentration of 10 mg/mL, and PEG was dissolved in distilled and deionized water (DDW) to prepare various concentrations of 2, 10 and 20 mg/mL. The catechin solution was mixed with each PEG solution in a volume ratio of methanol to DDW of 1:1, 1:5, and 1:10. Solutions mixed at catechin to PEG weight ratios of catechin/PEG 1 (CP1), catechin/PEG 5 (CP5) and catechin/PEG 10 (CP10) were mixed intensively for 15 minutes. Thereafter, the solution mixture was transferred to an evaporator and the remaining methanol was removed at 50° C. for 2 hours. The solution mixture was then filtered through a 0.4 μm filter and freeze-dried to produce a powder. Pure catechins and PEG were also subjected to the same procedure. For animal experiments, completely dried catechin/PEG, catechin or PEG powder was redissolved in saline (JW Pharmaceutical, Seoul, Korea) and their catechin concentration was adjusted to 10 mg/mL.

All eye-drops were prepared to 10 mL and dispensed into 1 mL vials and stored at −20° C. One vial was thawed daily, kept in the refrigerator and discarded after dripping of 5 times a day.

In the preparation of catechin/PEG nanocomposite using catechin and PEG, the reaction is as shown in the following Reaction Scheme 1.

[Reaction Scheme 1]

-continued

Example 2: Mouse Model of Dry Eye Syndrome

Animal protection and all experimental procedures were carried out in accordance with recommendations by the Institutional Animal Care and Use Committee (No. IJUBPH 2016-005-05) and the ARVO (Association for Research in Vision and Ophthalmology for the use of animals in ophthalmic and vision research) according to the guidelines for animal experiments at Inje University Busan Paik Hospital.

Eighty three NOD.B10.H2$^b$ mice (6 weeks old) in total were obtained from the Jackson Laboratory (Bar Harbor, Me., USA) and performed an acclimatization process for 6 to 10 weeks. Mice were kept in a semi-pathogen free (SPF) facility, and feed and water were provided as free feed.

Six mice were used for histopathological analysis as a baseline. Seventy seven mice were injected subcutaneously four times daily for 10 days with 500 μg/200 μL of scopolamine hydrobromide (Sigma-Aldrich) which is a muscarinic receptor blocker. At this time, the mice were exposed to desiccation stress (DS) for 10 days, including air ventilation by the fan, with an average ambient humidity of 40% or less for 18 hours daily. On day 10 after scopolamine hydrobromide injection and dryness stress exposure, tear production was measured and a photograph of the cornea was taken.

As a result, at least 65% of tears were decreased in all mice when compared with baseline, and eye dryness symptoms were shown with the increase of at least grade 2 of corneal disorder score.

On day 10 of DS, 11 mice were used for histopathological analysis. Sixty six mice were randomly divided into six groups: vehicle (n=11, saline of 5 μL), catechin group (n=11, 1% catechin of 5 μL), CP1 group (n=11, 1% CP1 5 μL), CP5 group (n=11, 1% CP5 5 μL), CP10 group (n=11, 1% CP10 5 μL) and PEG group (n=11, 1% PEG 5 μL). All treatments were performed by injecting five times a day and the amount of tear, corneal disorder and fluorescein scores were measured at baseline, day 10 of DS, and day 3, 5, 7, and 10 after treatment. Hematoxylin and eosin (H&E) and PAS (periodic acid Schiff) staining were performed on the cornea and conjunctiva, respectively. In addition, expression of inflammatory factors associated with immunohistochemical staining in the lacrimal gland was evaluated.

Example 3: Tear Production Analysis

The amount of tears was measured with reference to a previously reported paper (*Eye Contact Lens.* 2006; 32(6): 272-276). Briefly, the phenol red-impregnated cotton threads (Zone-Quick, Oasis, Glendora, Calif., USA) were placed in the lateral canthus and after 20 seconds, the thread turned red by wet tears was observed with a stereoscopic zoom microscope (SZX7, Olympus Corp., Tokyo, Japan). The amount of tears was calculated by comparison with a standard curve expressed using a basic solution (1.5 L of 0.9% saline and 5 mL of 5 N sodium hydroxide (NaOH)).

Figure 1:
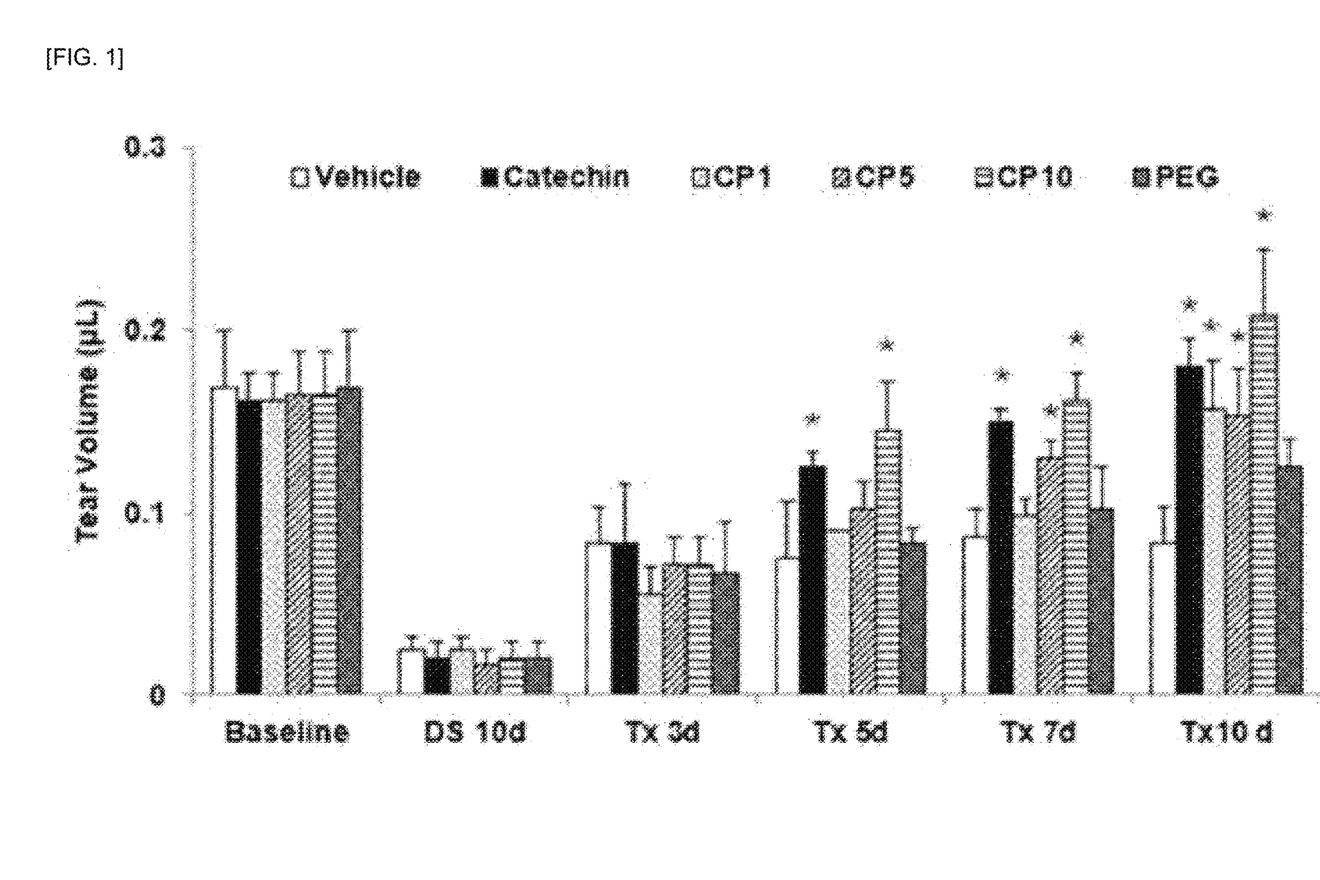
FIG. 1 shows the effect of PEG/catechin nanocomposite on tear production in a mouse model of dry eye syndrome and result of measuring the amount of tears on baseline, on day 10 after desiccation stress, on day 3~10 after catechin, catechin/PEG nanocomposite (CP1, CP5 and CP10) or PEG treatment using phenol red-impregnated cotton threads.

As a result, referring to FIG. 1, the amount of tears in the baseline of NOD.B10.H2$^b$ mouse was measured to be 0.16±0.02 μL, and it was confirmed that the amount of tears was significantly reduced to 0.02±0.01 μL by the drying stress. However, after 5 days of catechin and CP10 treatment, the amount of tears was significantly increased to 0.13±0.01 μL and 0.15±0.03 μL, respectively. Treatment of catechin/PEG nanocomposite also increased the tear production in a dose-dependent manner. Compared with day 10 of DS, the catechin-treated group showed a time-dependent increase in tear production after 3 days (0.08±0.03 μL) of treatment, and recovered to the baseline level after 5 days of treatment. Compared with day 10 of DS, the CP1 treated group significantly increased the tear production after 5 days of treatment and recovered to the baseline level after 10 days of treatment (0.16±0.03 μL). In addition, compared with day 10 of DS, CP5 treated group significantly increased the tear production after 3 days of treatment (0.10±0.02 μL), and recovered to the baseline level after 7 days of treatment (0.13±0.01 µL). The amount of tear in the CP10 treated group was statistically significant after 3 days of treatment (0.07±0.02 µL) and recovered to the baseline level after 5 days of treatment. However, the tear production tended to increase in the PEG-treated group, but there was no significant difference when compared to the vehicle.

Example 4: Analysis of Corneal Irregularities

Corneal abnormality was measured with reference to a previously reported paper (*Invest Ophthalmol Vis Sci.* 2006; 47:2847-2856). On day 10, the white ring image of the corneal surface was observed on 2 hours after the last scopolamine hydrobromide injection and on 1 hour after the last dripping of the catechin and catechin/PEG nanocomposite eye drops under optical fiber ring illumination using a stereoscopic zoom microscope. Corneal smoothness was assessed by grading the irregularity of the corneal epithelial cells reflected in the white ring of the digital image. The reflected ring was divided into quarters and the corneal disorder score was calculated using the 5-point scale based on the number of distorted branches in the reflected ring: 0, no distortion; 1, a quarter of distortion; 2, two-quarters of distortion; 3, three-quarters of distortion; 4, four-quarters of distortion; 5, severe distortion.

Figure 2:
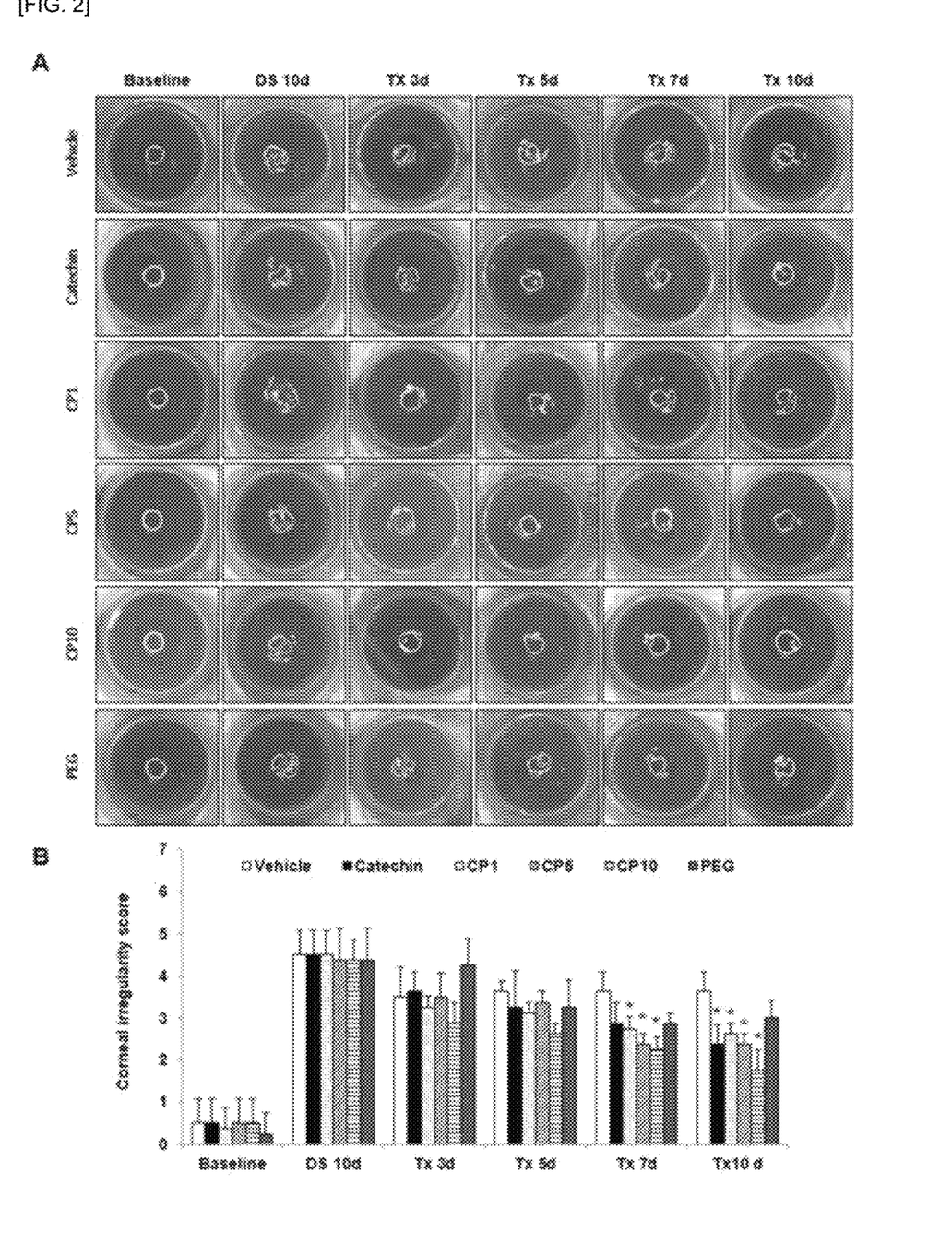
FIG. 2 shows the effect of the catechin/PEG nanocomposite on the corneal disorder. (A) is a microscopic image of a white ring on the corneal surface and (B) is a scored result of corneal disorder.

As a result, referring to FIG. 2A, the dryness stress gradually increased the corneal disorder in all groups. However, in the catechin/PEG nanocomposite and catechin treatment groups, white rings were observed on day 7 and day 10 after treatment, respectively. The vehicle and PEG-treated groups were confirmed not to improve the distorted white ring even on day 10 after treatment. The corneal disorder scores and comparison data within & between groups were shown in FIG. 2B. When compared with the baseline (0.44±0.55), it was confirmed that the corneal disorder score gradually increased to 4.44±0.62 by the dryness stress.

Compared with the vehicle-treated group (3.63±0.48), the CP1 treated group, the CP5 treated group and the CP10 treated group showed a significant decrease in the corneal disorder score to 2.75±0.29, 2.38±0.25, and 2.25±0.30 on day 7 after treatment, respectively. However, catechin-treated group showed no statistically significant difference on day 7 after treatment (2.88±0.48) when compared with vehicle-treated group, and significantly decreased corneal disorder on day 10 after treatment (2.38±0.47). The PEG-treated group showed a tendency to decrease corneal disorder, but there was no significant difference when compared to the vehicle. In addition, there was no statistically significant difference in corneal disorder in the vehicle-treated group when compared with on day 10 of DS.

Example 5: Corneal Fluorescence Staining Assay

Fluorescence staining of the cornea was performed with reference to a previously reported paper (*CLAO J.* 1995; 21: 221-232). The lateral conjunctival sac of the mouse was treated with 1 µL of 5% fluorescein and the eyes were examined under a cobalt blue illumination using a slit lamp biomicroscopy (SL-D7; Topcon Medical Systems, Inc., Oakland, N.J.). Punctate staining was assessed using a standard NEI (national eye institute) grading system with scores of 0 to 3 on each of the five areas of the cornea.

Figure 3:
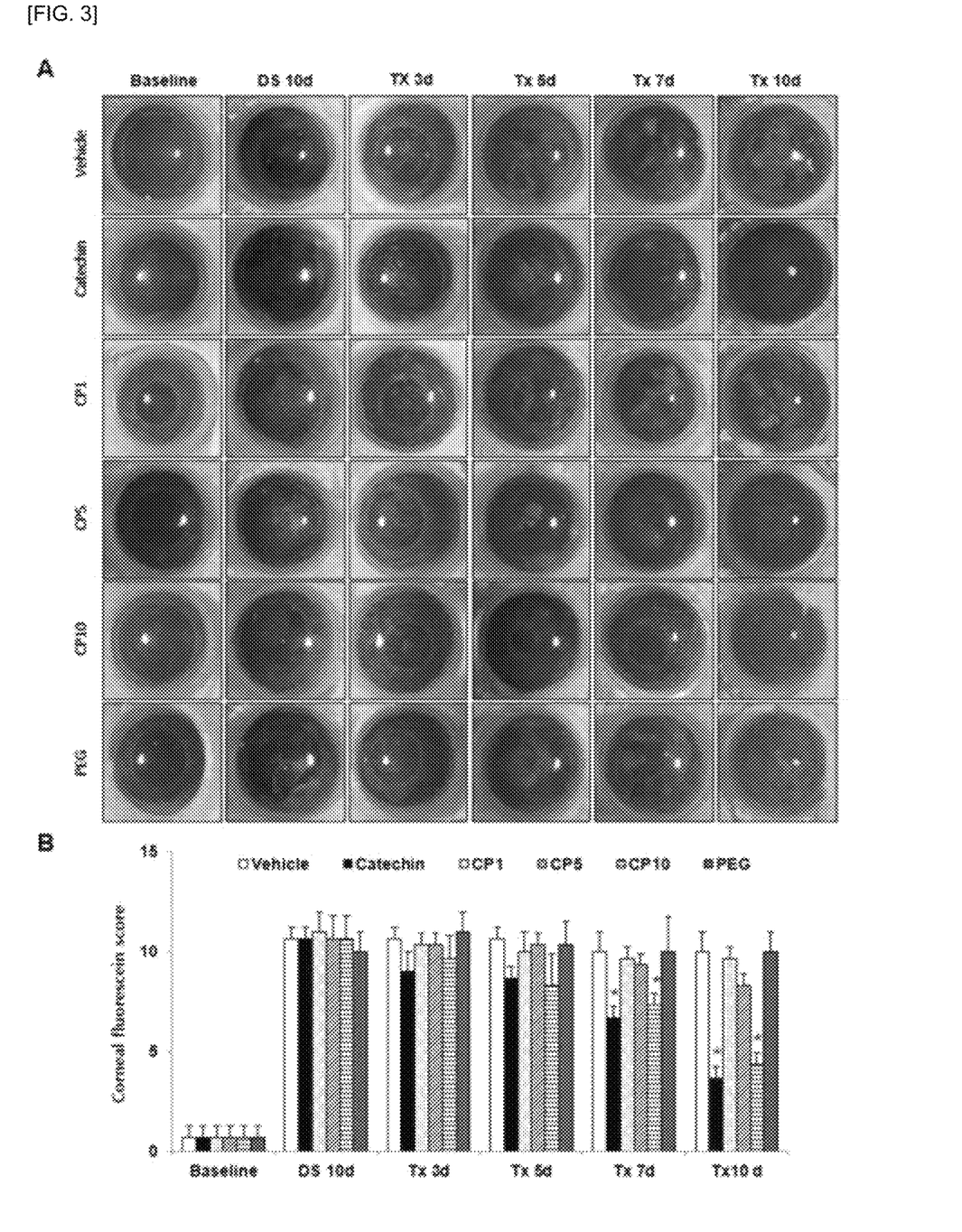
FIG. 3 shows the effect of the catechin/PEG nanocomposite on the corneal fluorescence staining. (A) is biomicroscope image with corneal fluorescence staining and (B) is a scored result of corneal fluorescence staining.

As a result, referring to FIG. 3, it was confirmed that fluorescence staining of the cornea was significantly increased to 10.61±0.91 due to drying stress. However, catechin-treated group (6.67±0.58) and CP10 treated group (7.33±0.57) were significantly decreased on day 7 after treatment and statistically significantly different from vehicle-treated group (10.00±1.00). On day 10 after treatment, there was no statistically significant difference in corneal fluorescence staining scores between catechin-treated group (3.67±0.58) and CP10 treated group (4.33±0.58). All treatment groups except catechin-treated group and CP10-treated group showed no statistically significant difference from the vehicle-treated group.

Example 6: Histopathological Analysis

Surgically resected orbits of mice were fixed in 10% formalin and embedded with paraffin. Paraffin tissue was micro-sectioned with a microtome (RM2245, Leica Biosystems, Nussloch, Germany) to obtain a 5 µm cornea section, followed by hematoxylin and eosin staining. In addition, PAS staining of conjunctival goblet cells was performed according to the protocol provided using a commercial kit (Merck, Darmstadt, Germany). The stained sections were photographed using a virtual microscope (NanoZoomer 2.0 RS, Hamamatsu, Japan).

Figure 4:
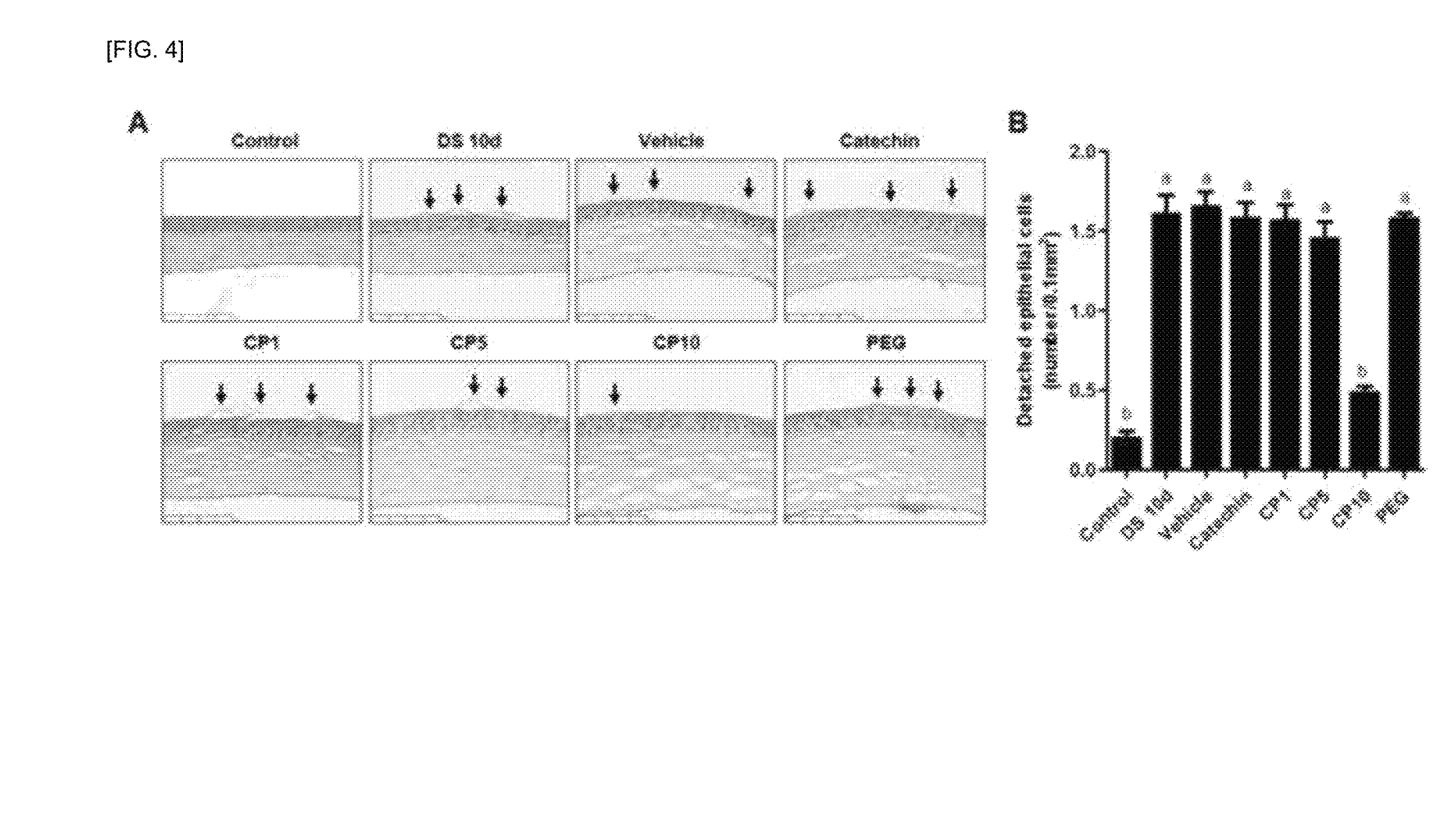
FIG. 4 shows the effect of the catechin/PEG nanocomposite on the corneal epithelial cell detachment. (A) is the corneal epithelial cells detached by cornea section with hematoxylin and eosin (H&E) staining and (B) is the result of quantifying the number of corneal epithelial cells which was detached.

FIG. 4A is the result of staining the mouse cornea section with hematoxylin and eosin at the baseline, day 10 of DS, and day 10 after treatment. On day 10 of DS, detached epithelial cells were observed more frequently, whereas CP10 treated group decreased the number of detached epithelial cells. FIG. 4B shows quantitatively the number of corneal epithelial cells detached per 0.1 mm$^2$. Dryness stress significantly increased the corneal epithelial cell detachment to 1.60±0.35/0.1 mm$^2$, whereas CP10 treated group (0.48±0.12) significantly reduced the corneal epithelial cell detachment to the baseline level. All treatment groups except CP10 group showed no statistically significant difference with day 10 of DS.

Figure 5:
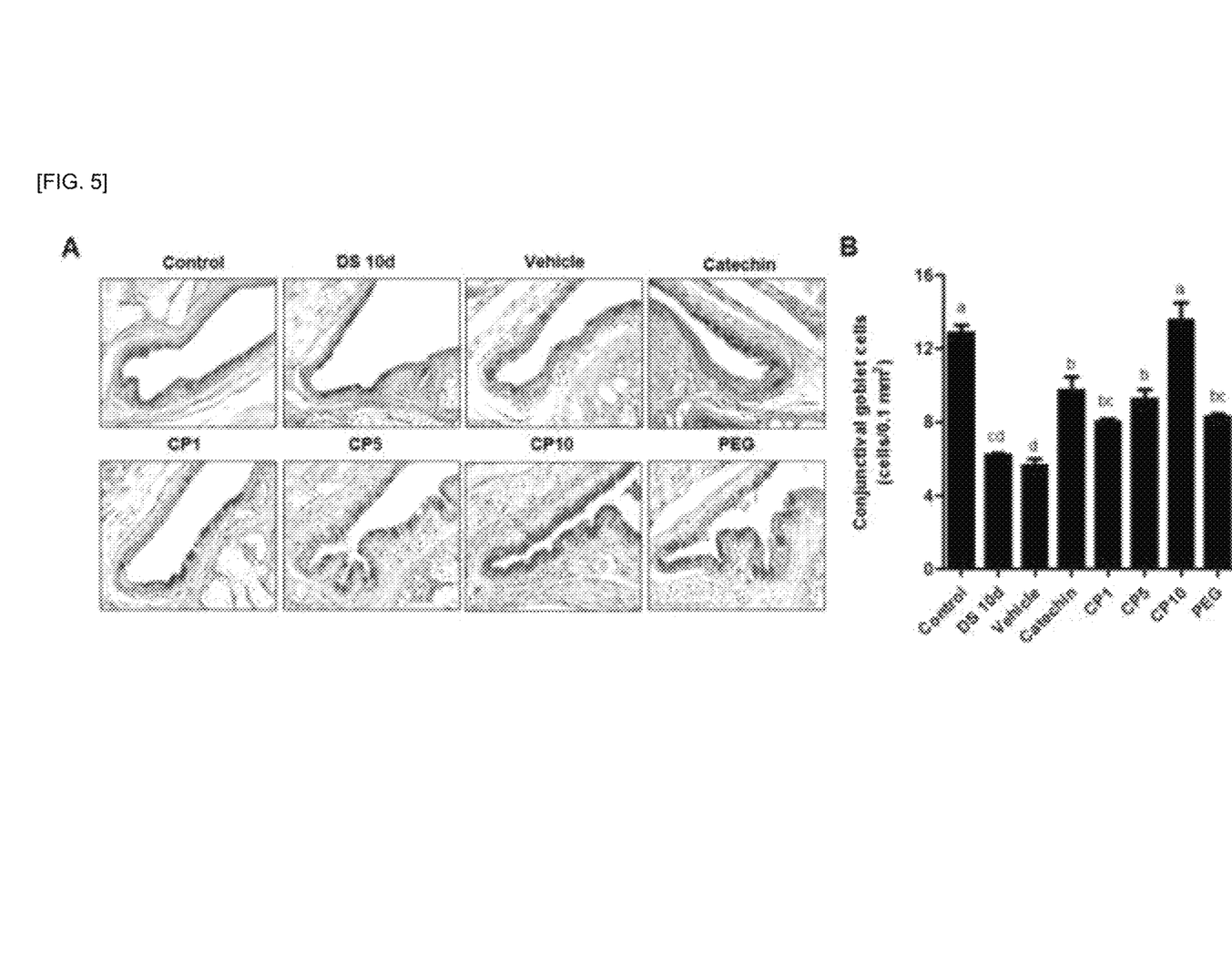
FIG. 5 shows the effect of the catechin/PEG nanocomposite on the density of conjunctival goblet cells. (A) is conjunctival goblet cells with PAS (periodic acid Schiff) staining of and (B) is the result of quantifying the density of conjunctival goblet cells.

FIG. 5A shows that the inferior fornix conjunctiva of NOD.B10.H2$^b$ mouse was stained with PAS, confirming that the conjunctival goblet cells had a strong purple color. As shown in FIG. 5B, the number of conjunctival goblet cells in the control mice was 12.86±0.76/0.1 mm$^2$, but it was found to be gradually decreased to 6.19±0.16/0.1 mm$^2$ by the dryness stress. However, in the catechin-treated group, the CP1 treated group, and the CP5 treated group, the number of conjunctival goblet cells was significantly increased to 9.71±1.25/0.1 mm$^2$, 8.00±0.29/0.1 mm$^2$ and 9.24±0.87/0.1 mm$^2$, respectively. However, there was no statistically significant difference in the number of conjunctival goblet cells between these groups, and it was not recovered to the control level. PEG-treated group increased the number of conjunctival goblet cells to 8.29±0.28/0.1 mm$^2$, similar to that of CP1-treated group. CP10 treated group significantly increased the number of conjunctival goblet cells to 13.52±1.67/0.1 mm$^2$ (DS 10 days), similar to that of the control group. The number of conjunctival goblet cells in the vehicle-treated group was not statistically different from that on day 10 of DS.

Example 7: Immunohistochemistry (IHC) Analysis

Surgically resected lacrimal glands were fixed in 10% formalin and embedded in paraffin. Paraffin tissue was micro-sectioned with a microtome to prepare a 5 µm slice. The paraffin sections were deparaffinized, rehydrated, heat treated in an antigen retrieval solution, and then immersed in 3% hydrogen peroxide solution for 30 minutes. As shown in Table 1, paraffin sections were reacted with specific primary antibodies for 1 hour at room temperature, then washed and reacted with secondary antibodies (Dako Corp., Glostrup, Denmark) for 40 minutes. The paraffin sections were visualized with 3-3'-diaminobenzidine (DAB) as a chromogen and stained for contrast with hematoxylin (Mayer's hematoxylin, Sigma, St. Louis, Mo., USA) for 30 seconds. The images of the sections were photographed using a virtual microscope.

TABLE 1

| Antigen | Type[†] | Dilution | Manufacturer[‡] | Catalog No. |
|---|---|---|---|---|
| ICAM-1 | MM | 1:200 | Millipore | MAB2130 |
| IL-1β | RbP | 1:500 | Abcam | ab9722 |
| IL-6 | RbP | 1:500 | Abcam | ab7737 |
| IL-17 | RbP | 1:200 | Abcam | Ab79056 |
| MMP-2 | RbP | 1:200 | Abcam | ab37150 |
| MMP-9 | RbP | 1:200 | LifeSpan | LS-B2486-50 |
| TNF-α | RbP | 1:200 | Abcam | ab66579 |
| VCAM-1 | RbP | 1:200 | Bioss | bs-0920R |

Figure 6:
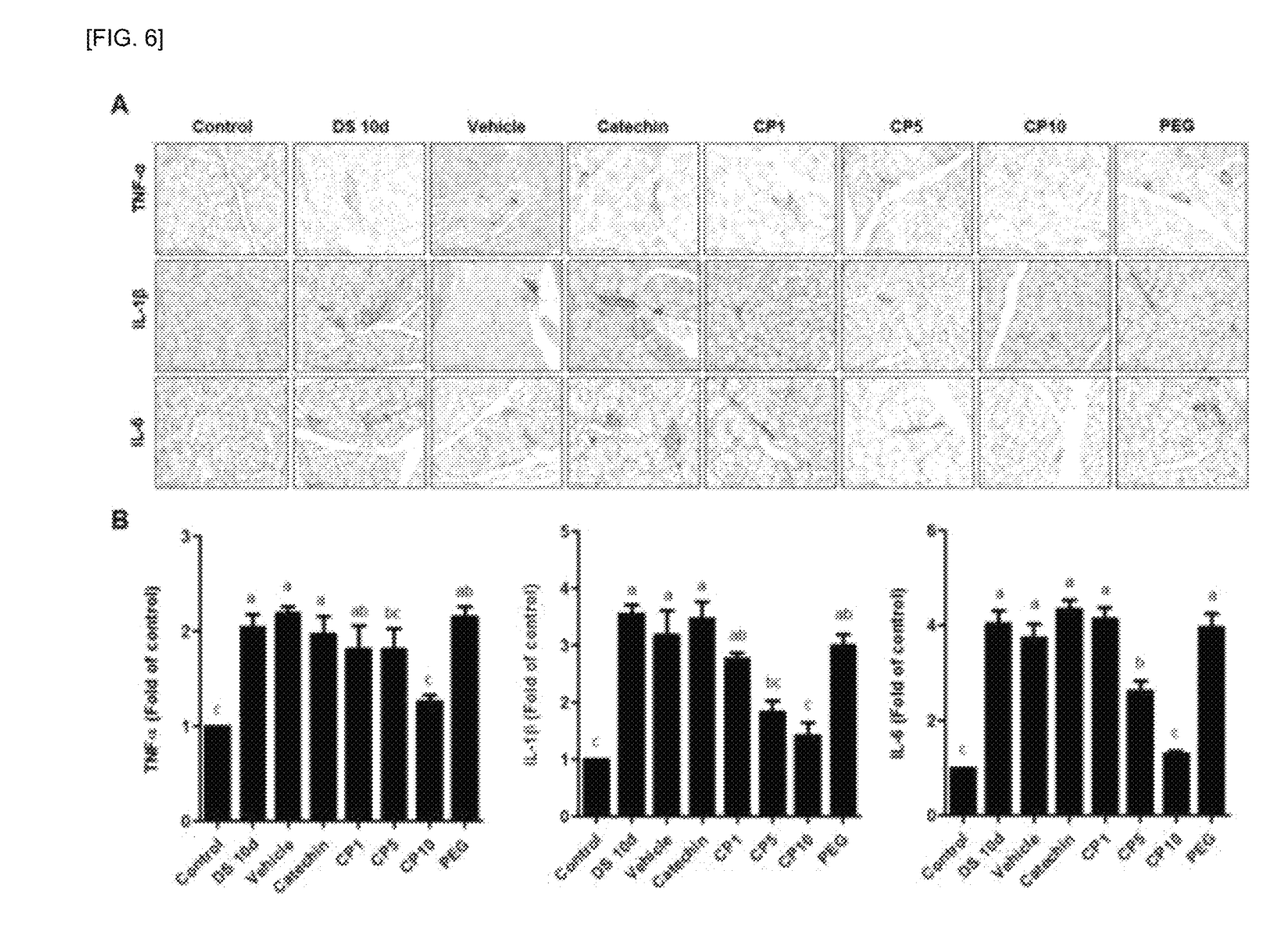
FIG. 6 shows the effect of the catechin/PEG nanocomposite on the expression of inflammatory cytokines in the lacrimal gland. (A) shows the expression of IL-1β, IL-6 and TNF-α by immunostaining using a lacrimal section. (B) is the result of quantifying the expression.

As a result, FIG. 6A shows a result of immunostaining a lacrimal gland section with a pro-inflammatory cytokine antibody. Referring to FIG. 6B, the expression of TNF-α, IL-1β and IL-6 by dryness stress was significantly increased to 2.04 times, 3.55 times, and 4.02 times, respectively, when compared with the control group. It was confirmed that CP10 treated group inhibited the expression of the pro-inflammatory cytokine to a control level. In contrast, the catechin-treated group showed no statistically significant difference with day 10 of DS. CP1 treated group and PEG treated group also did not affect the expression of pro-inflammatory cytokine.

Figure 7:
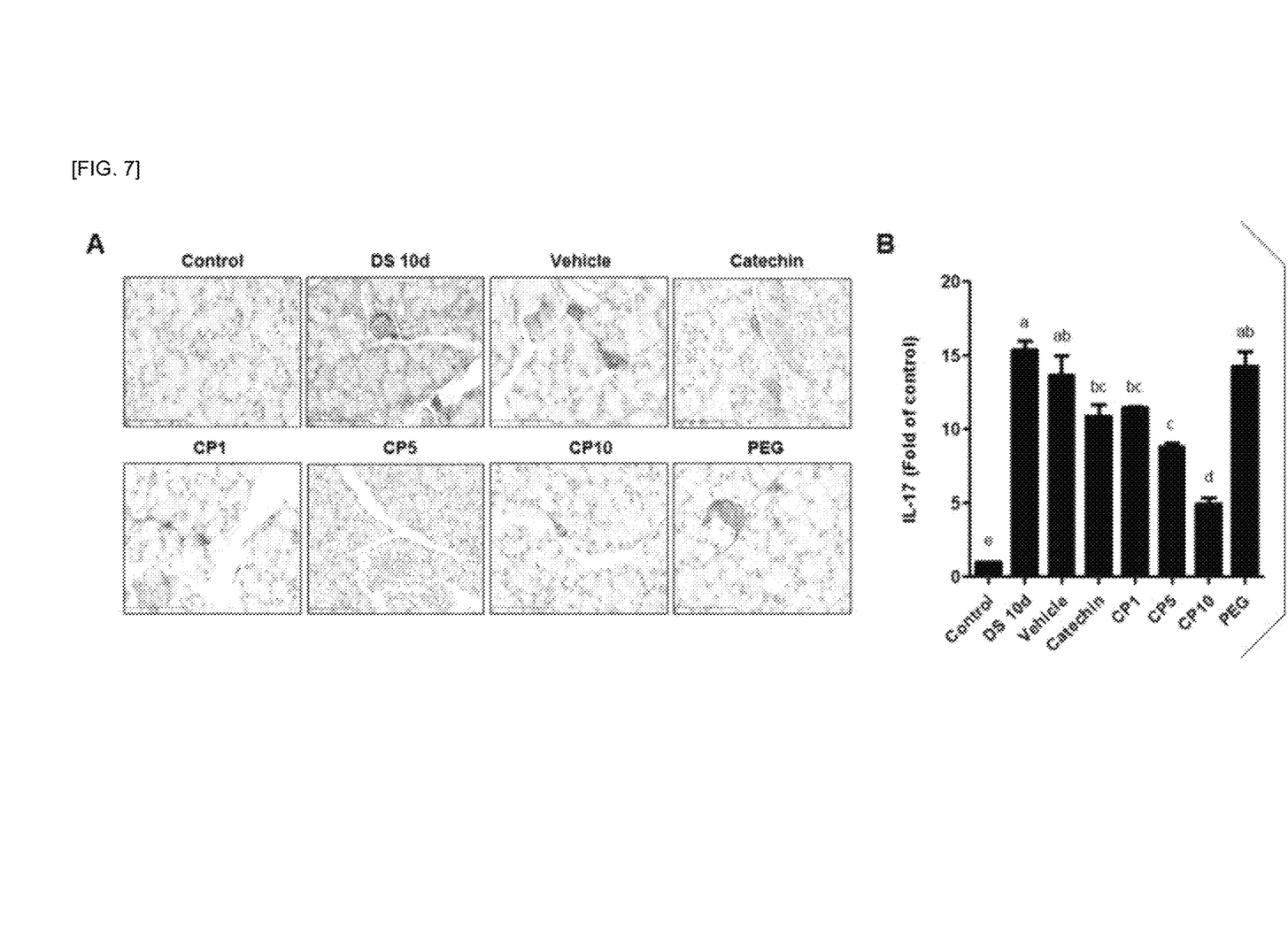
FIG. 7 shows the effect of the catechin/PEG nanocomposite on the IL-17 expression in the lacrimal gland. (A) shows the expression of IL-17 by immunostaining using a lacrimal section. (B) is the result of quantifying the expression.

Also, referring to FIG. 7, it was confirmed that IL-17 expression by dryness stress in the lacrimal gland sections was increased by 15.35 times as compared with the control group. However, all treatment groups of catechin-treated and catechin/PEG nanocomposites significantly decreased IL-17 expression in a PEG dose-dependent manner. CP10 treated group significantly reduced IL-6 expression in the lacrimal gland section by 68%, and IL-6 expression was not affected by the vehicle-treated group and the PEG-treated group.

Figure 8:
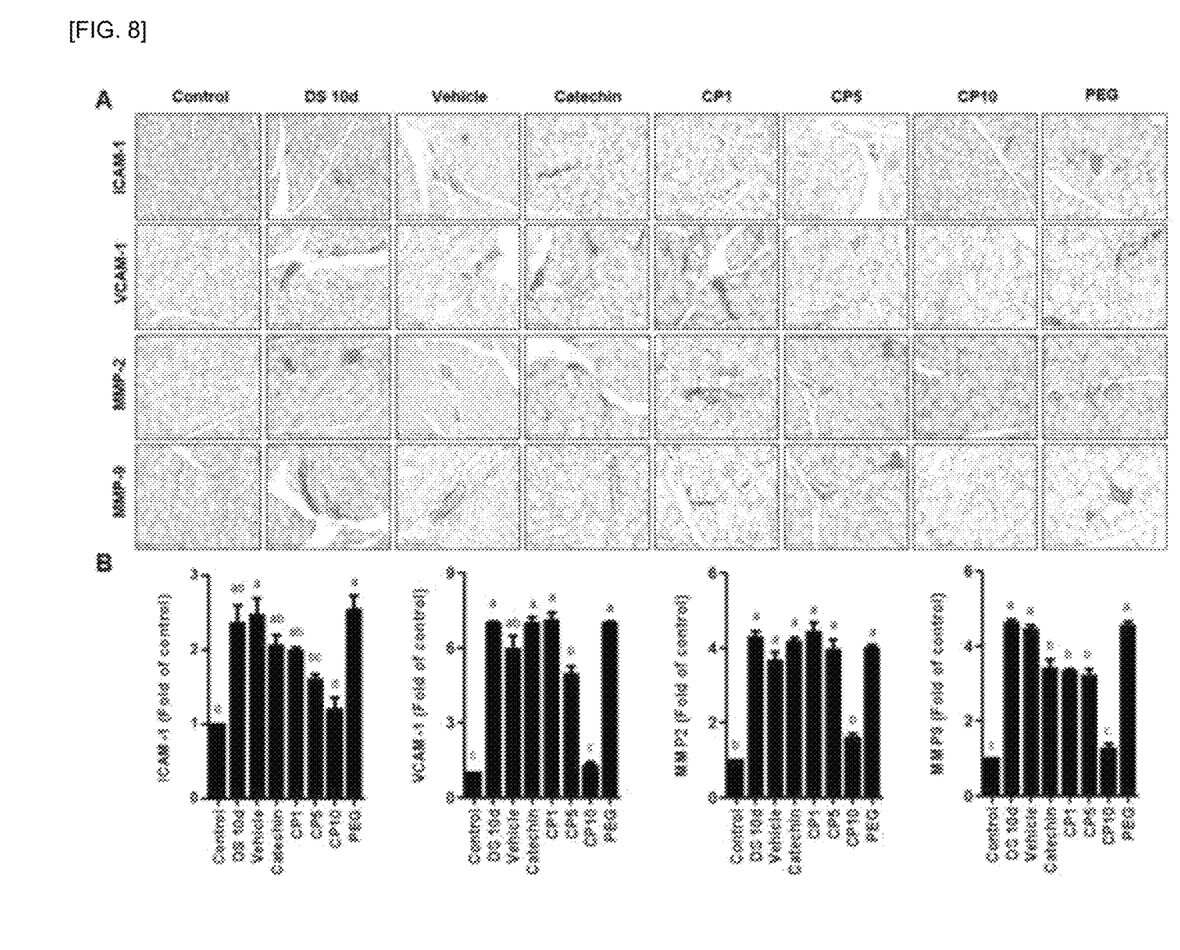
FIG. 8 shows the effect of the catechin/PEG nanocomposite on adhesion molecules and matrix metalloproteinases (MMPs), (A) shows the expression of ICAM-1, VCAM-1, MMP-2 and MMP-9 by immunostaining using a lacrimal section. (B) is the result of quantifying the expression.

In addition, referring to FIG. 8, the expression of adhesion molecules such as ICAM-1 (intercellular adhesion molecule-1) and VCAM-1 (vascular cell adhesion molecule-1) by dryness stress was increased 2.36 times and 6.98 times, respectively, when compared with the control group. In the catechin-treated group, the CP1-treated group and the CP5-treated group, the expression of the adhesion molecules did not show statistically significant difference with day 10 of DS and the vehicle-treated group. However, the CP10-treated group was found to significantly reduce the expression of ICAM-1 and VCAM-1 to the control level (1.20 and 1.26 times of the control group, respectively). In addition, dryness stress gradually increased the expression of matrix metalloproteinase (MMP), MMP-2 and MMP-9, in the lacrimal gland sections (4.27 and 4.61 times of the control group, respectively). All treatment groups except the CP10 treated group did not affect the expression of MMP-2, and only the CP10 treated group significantly reduced the expression of MMP-2 to the control level (62.76% of the day 10 of DS). The CP10 treated group also significantly decreased the expression of MMP-9 to the control level (72% of the day 10 of DS), and the vehicle-treated group and the PEG-treated group did not affect it. Compared with the day 10 of DS, catechin-treated, CP1-treated, and CP5-treated groups significantly decreased the MMP-9 expression but did not recover to the control level.

Example 8: Statistical Analysis

Data were analyzed using SPSS version 22.0 (SPSS, Chicago, Ill., USA) and expressed as mean±standard deviation (SD). The difference between the groups was analyzed using one-way ANOVA and defined as statistically significant when the P value was less than 0.05 for Tukey's test.

As described above in detail a specific part of the present invention, it is apparent to those skilled in the art that the specific technology is only a preferred embodiment, which is not intended to limit the scope of the present invention. Accordingly, the actual scope of the present invention will be defined by the appended claims and their equivalents.

The scope of the present invention is defined by the appended claims, and all changes or modifications derived from the meaning and scope of the claims and their equivalents should be construed as being included within the scope of the present invention.

The invention claimed is:

1. A method of treating dry eye syndrome in a subject in need thereof, comprising:
   providing a pharmaceutical composition comprising a nanocomposite composed of a catechin and a polyethylene glycol as an active ingredient; and
   administering the pharmaceutical composition to the subject, wherein the dry eye syndrome is treated,
   wherein the nanocomposite is represented by a following Chemical Formula 1:

[Chemical Formula 1]

wherein R1 to R4 are the same or different from each other and are hydrogen or the catechin, and m is any one integer of 8 to 460.

2. The method of claim 1, wherein the nanocomposite is prepared by mixing a catechin solution and a polyethylene glycol solution at a weight ratio of 1:1 to 15.

3. The method of claim 1, wherein the nanocomposite has an average diameter of 100 to 200 nm.

4. The method of claim 1, wherein the nanocomposite increases tear production and density of conjunctival goblet cells.

5. The method of claim 1, wherein the nanocomposite reduces corneal epithelial cell detachment, adhesion molecules, pro-inflammatory cytokines and matrix metalloproteinases (MMP).

6. The method of claim 5, wherein the adhesion molecules are intercellular adhesion molecule-1 (ICAM-1) and vascular cell adhesion molecule-1 (VCAM-1), and the pro-inflammatory cytokines are TNF-α, IL-1β, IL-6 and IL-17, and the matrix metalloproteinases are MMP-2 and MMP-9.

7. The method of claim 1, wherein the pharmaceutical composition is provided by mixing the nanocomposite with a pharmaceutically acceptable carrier and providing the composition as eye drugs or injections in form of eye drops, or eye ointment or injection in form of gel.

8. A method of preparing a nanocomposite composed of a catechin and a polyethylene glycol comprising:
   a first step of preparing a catechin solution by dissolving the catechin in a C1 to C4 alcohol;

a second step of preparing a polyethylene glycol solution by dissolving polyethylene glycol in water;

a third step of preparing a mixture by mixing the catechin solution of the first step and the polyethylene glycol solution of the second step;

a fourth step of removing the C1 to C4 alcohol from the mixture; and a fifth step of filtering the mixture from which the C1 to C4 alcohol is removed by a filter, wherein the nanocomposite is represented by a following Chemical Formula 1:

[Chemical Formula 1]

wherein R1 to R4 are the same or different from each other and are hydrogen or the catechin, and m is any one integer of 8 to 460.

9. The method of claim 8, wherein in the third step, the catechin solution and the polyethylene glycol solution are mixed at a weight ratio of 1:1 to 15.

10. The method of claim 8, wherein the fourth step is performed at 40 to 60° C. for 1 to 3 hours.

11. The method of claim 8, wherein the nanocomposite has an average diameter of 100 to 200 nm.

* * * * *